US00PP36734P2

(12) United States Plant Patent
Townsend

(10) Patent No.: US PP36,734 P2
(45) Date of Patent: Jun. 10, 2025

(54) HOP PLANT NAMED 'IH151343'

(50) Latin Name: ***Humulus lupulus* L.**
Varietal Denomination: IH151343

(71) Applicant: Oregon State University, Corvallis, OR (US)

(72) Inventor: Michael Shaun Townsend, Corvallis, OR (US)

(73) Assignee: Indie Hops, LLC, Portland, OR (US)

( * ) Notice: Subject to any disclaimer, the term of this patent is extended or adjusted under 35 U.S.C. 154(b) by 0 days.

(21) Appl. No.: 18/785,548

(22) Filed: Jul. 26, 2024

(51) Int. Cl.
*A01H 5/02* (2018.01)
*A01H 6/28* (2018.01)

(52) U.S. Cl.
USPC ..... Plt./236
CPC ..... *A01H 6/28* (2018.05)

(58) Field of Classification Search
USPC ..... Plt./236
CPC ..... A01H 6/28; A01H 5/02
See application file for complete search history.

*Primary Examiner* — Keith O. Robinson
(74) *Attorney, Agent, or Firm* — Klarquist Sparkman, LLP

(57) ABSTRACT

A new and distinct hop plant cultivar named 'IH151343' is disclosed, characterized by its tolerance to downy and powdery mildews, concentration of beta acids, oil content, and essential oil profile.

4 Drawing Sheets

Genus and species: *Humulus lupulus* L.
Variety denomination: 'IH151343'.

BACKGROUND

The present disclosure comprises a new and distinct cultivar of *Humulus lupulus* L., hereinafter referred to by the cultivar name 'IH151343'.

The new hop plant was derived from seed collected from a cross of female hop plant 'Hersbrucker Pure' (unpatented) and male hop plant '1218-2M' (unpatented; unreleased). 'Hersbrucker Pure' was developed in Huell, Germany and released in the 1980s. The male parent was developed in Corvallis, Oregon. The cross was made in July 2014 and the resulting hop plant was selected in February 2015 while growing in a greenhouse in Corvallis, Oregon.

SUMMARY

In July 2014 a cross was made between the female parent 'Hersbrucker Pure' and the male parent '1218-2M' at a farm research facility in Corvallis, Oregon. 'Hersbrucker Pure' is a publicly available hop cultivar that was developed and released in the 1980s. The male parent, '1218-2M', was developed in Corvallis, Oregon and is not publicly available. In January 2015, hand-collected seed was stratified for 8 weeks at 34° F. The seed was then planted in flats containing a standard soil mix, and were moved to a greenhouse. Established hop seedlings were evaluated for general vigor and powdery mildew (*Podosphaera macularis* [Wallr.]) resistance. 'IH151343' was one of the seedlings that were selected and transplanted into 1-gallon pots. Established potted plants were placed under a 6-foot short trellis system in June 2015 in a field nursery near Corvallis, Oregon. During the Summer of 2015, plants were evaluated for general vigor, sex, resistance to powdery and downy mildews (*Pseudoperonospora humuli* [Miyabe & Takah.]), and resistance to pests. Selected plants were transplanted into a field evaluation nursery under a standard 18-foot trellis in January 2016.

'IH151343' was determined to be a female genotype, and was further evaluated for downy and powdery mildew resistance in 2017, 2018, and 2019. Hop looper (*Hypnea humuli* Harris) resistance was evaluated in 2017, 2018, and 2019. Due to inconsistent pest pressure, 'IH151343' was evaluated for hop aphid (*Phorodon humuli* Schrank) resistance only in 2017 and 2019. Yield potential and preliminary sensory evaluations were determined in 2019.

Based upon agronomic performance and the initial sensory assessment, 'IH151343' was propagated via rhizomes obtained from the individual mother plant in January 2019 with additional propagation from stem cuttings in a greenhouse in Corvallis, Oregon. Under the direction and control of the inventor, plants were established in 1-gallon pots and transplanted into replicated field nurseries in Oregon's Willamette Valley during the Summer of 2020. These fields were managed using standard hop production techniques. Due to aggressive disease and pest control measures, only yield, chemistry, and sensory data were collected from these plots during the 2021, 2022, and 2023 growing seasons. Beginning in October 2021, 'IH151343' entered internal sensory evaluations utilizing dry rub and dry hop analyses.

'IH151343' can be distinguished from its male parent '1218-2M' at least on the basis that it only produces female flowers, whereas '1218-2M' only produces male flowers. In addition, 'IH151343' is more tolerant of downy and powdery mildews, and hop aphid pressure than '1218-2M'. However, 'IH151343' is less tolerant of hop looper pressure than male parent '1218-2M'.

The 'IH151343' hop variety is distinguished from other female hop varieties due to the following unique combination of agronomic and chemical characteristics. When grown in Oregon's Willamette Valley, 'IH151343':

1. Matures later than 'OR91331', but similar to female parent 'Hersbrucker Pure'.

2. Is more tolerant of downy and powdery mildews than 'Hersbrucker Pure'.
3. Yields similar to 'OR91331', but more than 'Hersbrucker Pure'.
4. Contains less alpha and beta acids than 'OR91331', but has a greater concentration of beta acids than 'Hersbrucker Pure'.
5. Contains less total oil than 'OR91331', but significantly more oil than 'Hersbrucker Pure'.
6. Contains differing amounts of 23 essential oil components implicated in beer flavor and aroma compared to 'OR91331' and 'Hersbrucker Pure'.

Asexual reproduction of the new hop variety 'IH151343' was first performed in Corvallis, Oregon via rhizomes in 2020. Subsequent propagations have been performed using both rhizomes and stem cuttings. Asexual reproduction of this new variety shows that the foregoing characteristics come true to form, are firmly fixed, and are established and transmitted through succeeding propagations.

DETAILED BOTANICAL DESCRIPTION

Figure 1:
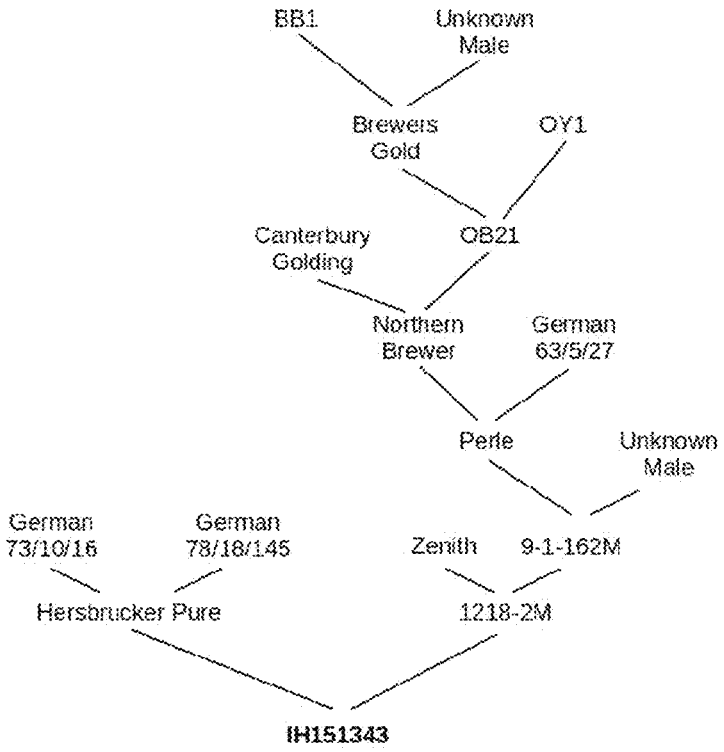
FIG. 1 illustrates the pedigree for 'IH151343'.
Figure 2:
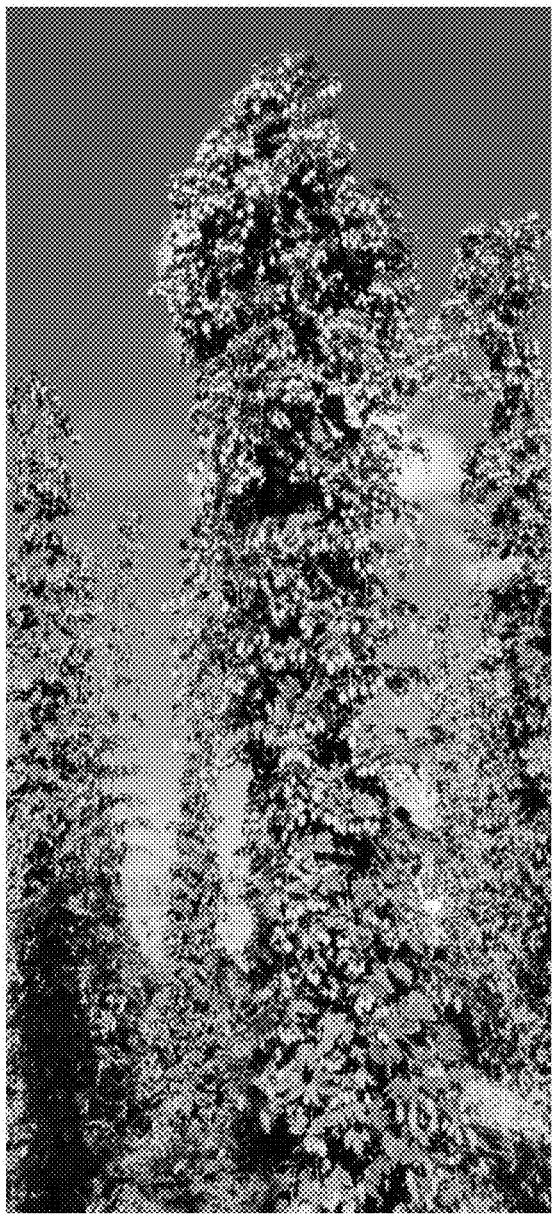
FIG. 2 shows a typical 3-year old 'IH151343' plant.
Figure 3:
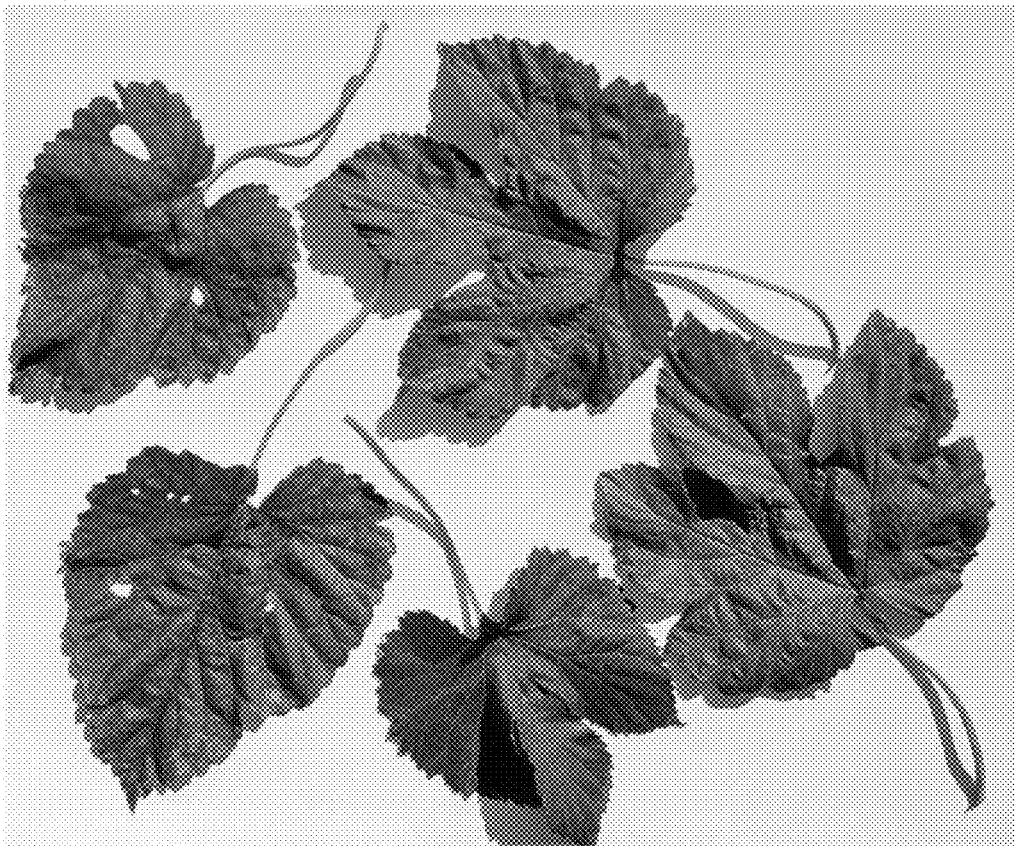
FIG. 3 shows the variable leaf lobing of 'IH151343'.
Figure 4:
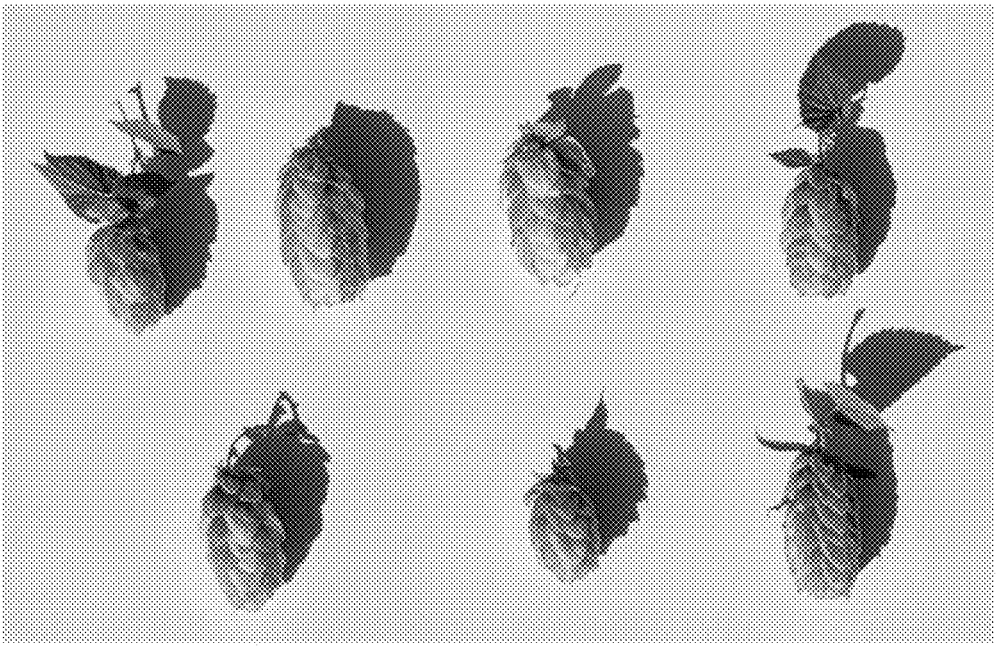
FIG. 4 shows the typical mature cones of 'IH151343'.

The following detailed description of the 'IH151343' cultivar is based on observations of various 2-4-year-old plants, 1$^{st}$ propagation generation, growing on a hop farm in Oregon's Willamette Valley between 2020 and 2023. The original mother plant has been observed growing in a cultivated area near Corvallis, Oregon. The new cultivar has not been evaluated under all possible environmental conditions but was developed for Oregon's Willamette Valley (USDA hardiness zone 8b near 45 degrees North latitude).

Certain characteristics of this cultivar such as growth, color, and cone chemical composition may vary with different grower practices and changing environmental conditions (e.g., light, temperature, moisture, nutrient availability, or other factors). Thus, the phenotype may vary somewhat with variations in environmental conditions without any variance in genotype. The color descriptions are all based on *The Royal Horticultural Society* (*R.H.S.*) *Colour Chart* (R.H.S.) 6$^{th}$ edition, 2015.

Parentage

Female parent: *Humulus lupulus* 'Hersbrucker Pure' (unpatented).

Male parent: *Humulus lupulus* '1218-2M' (unpatented).

Comparison to Other Varieties

Tables 1-3 provide comparisons among various traits for the cultivar 'IH151343', and the commercially available aroma hop cultivars 'OR91331' (U.S. Plant Pat. No. 31,042) and 'Hersbrucker Pure' (female parent). The aroma hop cultivar 'OR91331' was bred for the same target environment as 'IH151343' and targets hop forward, aromatic beer styles such as IPA (India Pale Ale). The aroma hop cultivar 'Hersbrucker Pure' was bred and released by the German Society of Hop Research in the early 1990s and is typically used in lighter, malt-forward beers such as lager and kolsch.

As shown in Table 1, 'IH151343' typically yields significantly more in Oregon's Willamette Valley than the female parent 'Hersbrucker Pure'. There is a numerical trend for 'IH151343' to yield slightly less than 'OR91331', but this was not statistically significant.

TABLE 1

Average per-plant yield for 'IH151343' over three years compared to the female parent 'Hersbrucker Pure' and popular aroma hop 'OR91331' when grown in Oregon's Willamette Valley.

| Cultivar | Yield (lbs)† | Range (lbs) |
|---|---|---|
| 'OR91331' | 10.84 a | 5.60-19.35 |
| 'IH151343' | 8.97 a | 6.24-11.82 |
| 'Hersbrucker Pure' | 6.40 b | 4.85-8.45 |

†Means followed by the same letter are not statistically significant at P = 0.05.

The alpha acids content, primary drivers of bitterness in hop, were highest in 'OR91331' (Table 2) with 'IH151343' being similar to female parent 'Hersbrucker Pure'. For beta acids and total oil, 'IH151343' is intermediate between 'OR91331' (highest) and the female parent 'Hersbrucker Pure' (lowest). Table 3 lists essential oil component concentrations for 23 compounds that potentially impact beer flavor and aroma. The chemistry data are for plants growing in Oregon's Willamette Valley, the targeted growing environment for 'IH151343'.

TABLE 2

Bittering acids and total oil content for 'IH151343', its female parent 'Hersbrucker Pure', and 'OR91331' averaged over three years (2021-2023) when grown in Oregon's Willamette Valley.

| Cultivar | Trait† | Range |
|---|---|---|
| | Alpha Acids (%) | |
| 'OR91331' | 12.57 a | 9.13-14.51 |
| 'Hersbrucker Pure' | 6.85 b | 6.10-7.33 |
| 'IH151343' | 6.48 b | 6.00-6.92 |
| | Beta Acids (%) | |
| 'OR91331' | 5.37 a | 3.98-6.23 |
| 'IH151343' | 3.11 b | 2.50-3.46 |
| 'Hersbrucker Pure' | 2.37 c | 2.19-2.54 |
| | Total Oil (mL/100 gm) | |
| 'OR91331' | 2.40 a | 1.39-3.00 |
| 'IH151343' | 1.43 b | 1.07-2.73 |
| 'Hersbrucker Pure' | 0.75 c | 0.66-0.90 |
| | Hop Storage Index | |
| 'Hersbrucker Pure' | 0.256 a | 0.242-0.274 |
| 'IH151343' | 0.255 a | 0.233-0.274 |
| 'OR91331' | 0.238 a | 0.222-0.278 |
| | Cohumulone (%) | |
| 'OR91331' | 21.00 a | 19.01-22.08 |
| 'Hersbrucker Pure' | 19.56 b | 18.21-20.40 |
| 'IH151343' | 19.52 b | 18.23-20.86 |
| | Colupulone (%) | |
| 'OR91331' | 40.56 a | 35.00-43.83 |
| 'Hersbrucker Pure' | 38.24 ab | 32.56-46.55 |
| 'IH151343' | 36.61 b | 32.00-40.39 |

†Means within a trait followed by the same letter are not statistically significant at P = 0.05.

TABLE 3

Essential oil component concentrations for three hop cultivars grown in Oregon's Willamette Valley. Data are mg/100 g dried tissue.

| Cultivar | Trait† | Range |
|---|---|---|
| | a-Pinene | |
| 'OR91331' | 2.25 a | 0.87-3.19 |
| 'IH151343' | 1.17 b | 0.65-2.53 |
| 'Hersbrucker Pure' | 0.70 b | 0.20-1.21 |
| | b-Pinene | |
| 'OR91331' | 22.21 a | 6.98-41.42 |
| 'IH151343' | 12.25 b | 6.45-23.85 |
| 'Hersbrucker Pure' | 7.85 b | 1.82-15.71 |
| | Myrcene | |
| 'OR91331' | 1490.69 a | 539.65-2380.36 |
| 'IH151343' | 832.40 b | 464.35-1778.60 |
| 'Hersbrucker Pure' | 488.67 b | 143.70-853.20 |
| | Limonene | |
| 'OR91331' | 8.90 a | 2.07-20.00 |
| 'IH151343' | 4.34 a | 1.83-8.07 |
| 'Hersbrucker Pure' | 3.23 a | 0.59-7.26 |
| | Cymene | |
| 'IH151343' | 11.17 a | 7.18-23.39 |
| 'OR91331' | 9.25 a | 3.99-15.97 |
| 'Hersbrucker Pure' | 3.19 b | 0.00-8.59 |
| | Methyl Heptanoate | |
| 'OR91331' | 19.73 a | 10.24-26.91 |
| 'IH151343' | 5.60 b | 1.79-9.94 |
| 'Hersbrucker Pure' | 3.84 b | 0.00-10.63 |
| | Linalool | |
| 'OR91331' | 19.84 a | 7.94-31.64 |
| 'IH151343' | 16.52 a | 10.68-29.55 |
| 'Hersbrucker Pure' | 6.09 b | 0.16-9.77 |
| | b-Caryophyllene | |
| 'OR91331' | 289.81 a | 162.31-446.81 |
| 'Hersbrucker Pure' | 108.40 b | 22.39-249.85 |
| 'IH151343' | 93.23 b | 66.03-159.29 |
| | Terpin-4-ol | |
| 'OR91331' | 0.88 a | 0.41-1.88 |
| 'IH151343' | 0.50 b | 0.16-1.11 |
| 'Hersbrucker Pure' | 0.03 b | 0.00-0.10 |
| | Farnesene | |
| 'IH151343' | 0.66 a | 0.00-1.54 |
| 'Hersbrucker Pure' | 0.65 a | 0.00-1.94 |
| 'OR91331' | 0.42 b | 0.00-1.16 |
| | Humulene | |
| 'OR91331' | 581.97 a | 358.50-835.14 |
| 'Hersbrucker Pure' | 240.53 b | 48.80-556.84 |
| 'IH151343' | 158.68 b | 108.37-265.61 |
| | Citral 1 | |
| 'Hersbrucker Pure' | 1.47 a | 0.00-4.01 |
| 'OR91331' | 0.57 a | 0.00-1.71 |
| 'IH151343' | 0.39 a | 0.14-0.87 |
| | Citral 2 | |
| 'Hersbrucker Pure' | 1.52 a | 0.06-3.74 |
| 'OR91331' | 0.58 b | 0.00-1.34 |
| 'IH151343' | 0.28 b | 0.15-0.47 |
| | a-Terpineol | |
| 'IH151343' | 2.75 a | 0.44-5.35 |
| 'Hersbrucker Pure' | 2.26 a | 0.20-5.79 |
| 'OR91331' | 1.57 a | 0.38-3.36 |

TABLE 3-continued

Essential oil component concentrations for three hop cultivars grown in Oregon's Willamette Valley. Data are mg/100 g dried tissue.

| Cultivar | Trait† | Range |
|---|---|---|
| | Geranyl Acetate | |
| 'OR91331' | 2.66 a | 0.26-5.55 |
| 'Hersbrucker Pure' | 0.60 b | 0.00-1.67 |
| 'IH151343' | 0.47 b | 0.14-0.81 |
| | Nerol | |
| 'OR91331' | 3.53 a | 0.18-6.44 |
| 'IH151343' | 3.03 a | 0.36-7.69 |
| 'Hersbrucker Pure' | 0.90 a | 0.04-1.92 |
| | Geraniol | |
| 'Hersbrucker Pure' | 6.37 a | 0.26-12.47 |
| 'OR91331' | 3.08 a | 0.34-8.28 |
| 'IH151343' | 2.36 a | 0.48-5.71 |
| | Caryophyllene Oxide | |
| 'IH151343' | 0.94 a | 0.06-2.87 |
| 'OR91331' | 0.88 a | 0.23-2.12 |
| 'Hersbrucker Pure' | 0.51 a | 0.00-1.42 |
| | Epoxide 1 | |
| 'OR91331' | 2.15 a | 0.66-4.42 |
| 'IH151343' | 0.97 b | 0.08-2.09 |
| 'Hersbrucker Pure' | 0.03 b | 0.34-0.34 |
| | Epoxide 2 | |
| 'Hersbrucker Pure' | 5.46 a | 0.61-10.32 |
| 'OR91331' | 2.32 ab | 0.36-4.95 |
| 'IH151343' | 1.13 b | 0.09-2.31 |
| | 3-Carene | |
| 'OR91331' | 9.08 a | 4.84-15.12 |
| 'IH151343' | 5.96 b | 3.32-11.31 |
| 'Hersbrucker Pure' | 1.28 b | 0.07-2.49 |
| | Methyl Geranate | |
| 'OR91331' | 5.99 a | 0.23-16.52 |
| 'IH151343' | 5.96 a | 3.32-11.31 |
| 'Hersbrucker Pure' | 1.28 a | 0.07-2.49 |
| | Geranyl Isobutyrate | |
| 'OR91331' | 40.93 a | 0.08-124.43 |
| 'IH151343' | 31.66 a | 0.52-92.26 |
| 'Hersbrucker Pure' | 6.66 a | 0.33-12.99 |

†Means within a trait followed by the same letter are not statistically significant at P = 0.05.

Tables 4 & 5 show various cone measurements in the lower and middle canopies of 'IH151343', 'Hersbrucker Pure', and 'OR91331'.

Summary of Lower Canopy Cone Measurements

Cones found in the lower canopy of 'IH151343' (Table 4):

1. have a larger bract width than either 'OR91331' or 'Hersbrucker Pure'
2. have a longer bract than 'Hersbrucker Pure'
3. have a wider bracteole than either 'OR91331' or 'IH151343'

Summary of Middle Canopy Cone Measurements

Cones found in the middle canopy of 'IH151343' (Table 5):

1. have longer and wider bracts than either 'OR91331' or 'Hersbrucker Pure'

2. have wider bracts than either 'OR91331' or 'Hersbrucker Pure', and a longer bract than 'Hersbrucker Pure'
3. have a longer cone and rachis than 'Hersbrucker Pure'

TABLE 4

Lower canopy cone measurements for 'IH151343', the female parent 'Hersbrucker Pure', and 'OR91331', an industry-standard aroma cultivar.

| Cultivar | Trait† | Range |
|---|---|---|
| Number of Bracts | | |
| 'OR91331' | 23.9 a | 22-28 |
| 'Hersbrucker Pure' | 23.00 a | 15-29 |
| 'IH151343' | 21.50 a | 16-28 |
| Number of Bracteoles | | |
| 'IH151343' | 39.2 a | 25-51 |
| 'OR91331' | 38.8 a | 31-47 |
| 'Hersbrucker Pure' | 35.5 a | 27-40 |
| Cone Bract Width (cm) | | |
| 'IH151343' | 1.2 a | 0.7-1.8 |
| 'OR91331' | 1.1 b | 0.5-1.8 |
| 'Hersbrucker Pure' | 0.8 c | 0.5-1.1 |
| Cone Bract Length (cm) | | |
| 'OR91331' | 1.7 a | 0.8-2.1 |
| 'IH151343' | 1.7 a | 1.2-2.0 |
| 'Hersbrucker Pure' | 1.5 b | 1.1-1.7 |
| Cone Bracteole Width (cm) | | |
| 'IH151343' | 1.1 a | 0.8-1.4 |
| 'OR91331' | 0.9 b | 0.5-1.8 |
| 'Hersbrucker Pure' | 0.8 c | 0.4-1.1 |
| Cone Length (cm) | | |
| 'IH151343' | 3.93 a | 2.8-4.8 |
| 'Hersbrucker Pure' | 3.48 a | 3.1-4.4 |
| 'OR91331' | 2.39 b | 2.2-2.8 |
| Rachis Length (cm) | | |
| 'OR91331' | 3.09 a | 2.6-4.0 |
| 'IH151343' | 3.05 a | 2.4-3.9 |
| 'Hersbrucker Pure' | 2.50 a | 2.1-2.9 |

†Means within a trait followed by the same letter are not statistically significant at P = 0.05.

TABLE 5

Middle canopy cone measurements for 'IH151343', the female parent 'Hersbrucker Pure', and 'OR91331', an industry-standard aroma cultivar.

| Cultivar | Trait† | Range |
|---|---|---|
| Number of Bracts | | |
| 'OR91331' | 27.3 a | 22-34 |
| 'Hersbrucker Pure' | 24.4 a | 21-28 |
| 'IH151343' | 24.4 a | 21-27 |
| Number of Bracteoles | | |
| 'OR91331' | 47.8 a | 36-68 |
| 'IH151343' | 47.5 a | 36-60 |
| 'Hersbrucker Pure' | 41.8 a | 38-48 |
| Cone Bract Width (cm) | | |
| 'IH151343' | 1.31 a | 0.7-1.9 |
| 'OR91331' | 1.02 b | 0.3-1.7 |
| 'Hersbrucker Pure' | 0.89 c | 0.3-1.3 |
| Cone Bract Length (cm) | | |
| 'IH151343' | 1.75 a | 1.1-2.1 |
| 'OR91331' | 1.60 b | 0.8-2.1 |

TABLE 5-continued

Middle canopy cone measurements for 'IH151343', the female parent 'Hersbrucker Pure', and 'OR91331', an industry-standard aroma cultivar.

| Cultivar | Trait† | Range |
|---|---|---|
| 'Hersbrucker Pure' | 1.38 c | 0.6-1.8 |
| Cone Bracteole Width (cm) | | |
| 'IH151343' | 1.1 a | 0.2-1.4 |
| 'OR91331' | 0.83 b | 0.5-1.2 |
| 'Hersbrucker Pure' | 0.79 b | 0.5-1.1 |
| Cone Length (cm) | | |
| 'OR91331' | 4.5 a | 3.5-5.6 |
| 'IH151343' | 4.4 a | 3.8-5.1 |
| 'Hersbrucker Pure' | 3.2 b | 2.8-3.5 |
| Rachis Length (cm) | | |
| 'IH151343' | 3.7 a | 3.0-4.6 |
| 'OR91331' | 3.4 a | 3.0-4.2 |
| 'Hersbrucker Pure' | 2.7 b | 2.4-3.1 |

†Means within a trait followed by the same letter are not statistically significant at P = 0.05.

Table 6 provides morphological measurements and compares 'IH151343' to female parent 'Hersbrucker Pure'. Compared to the female parent when grown in Oregon's Willamette Valley, 'IH151343' (Table 6):

1. has a longer main bine internode length
2. has a thicker main bine
3. has a longer sidearm
4. has a longer sidearm first internode length
5. has a longer leaf and cone petiole length

TABLE 6

Plant morphological measurements for 'IH151343' and its female parent 'Hersbrucker Pure' when grown in Oregon's Willamette Valley. Data are in cm.

| Cultivar | Trait† | Range |
|---|---|---|
| Main Bine Internode Length | | |
| 'IH151343' | 25.5 a | 17.7-29.5 |
| 'Hersbrucker Pure' | 16.9 b | 12.8-25.7 |
| Main Bine Diameter | | |
| 'IH151343' | 0.9 a | 0.6-1.1 |
| 'Hersbrucker Pure' | 0.3 b | 0.3-0.6 |
| Sidearm Length | | |
| 'IH151343' | 100.3 a | 44.5-182.0 |
| 'Hersbrucker Pure' | 22.6 b | 12.4-39.2 |
| Sidearm 1st Internode Length | | |
| 'IH151343' | 14.4 a | 9.3-18.4 |
| 'Hersbrucker Pure' | 8.2 b | 5.3-13.1 |
| Sidearm 1st Internode Width | | |
| 'IH151343' | 0.3 a | 0.2-0.4 |
| 'Hersbrucker Pure' | 0.3 a | 0.2-0.4 |
| Leaf Length | | |
| 'IH151343' | 10.9 a | 6.8-13.3 |
| 'Hersbrucker Pure' | 9.7 a | 8.7-10.6 |
| Leaf Width | | |
| 'IH151343' | 12.1 a | 7.3-15.2 |
| 'Hersbrucker Pure' | 11.1 a | 8.4-12.9 |
| Leaf Petiole Length | | |
| 'IH151343' | 7.5 a | 2.8-10.8 |
| 'Hersbrucker Pure' | 5.1 b | 4.1-6.1 |

TABLE 6-continued

Plant morphological measurements for 'IH151343' and its female parent 'Hersbrucker Pure' when grown in Oregon's Willamette Valley. Data are in cm.

| Cultivar | Trait† | Range |
|---|---|---|
| | Leaf Petiole Diameter | |
| 'IH151343' | 0.3 a | 0.1-0.4 |
| 'Hersbrucker Pure' | 0.3 a | 0.2-0.4 |
| | Cone Petiole Length | |
| 'IH151343' | 3.8 a | 2.0-5.5 |
| 'Hersbrucker Pure' | 1.9 b | 0.9-3.9 |
| | Cone Petiole Diameter | |
| 'IH151343' | 0.1 a | All 0.1 |
| 'Hersbrucker Pure' | 0.1 a | All 0.1 |

†Means within a trait followed by the same letter are not statistically significant at P = 0.05.

Additional Description

Additional data for 'IH151343' are presented in Table 7.

TABLE 7

Qualitative mid-canopy data collected from hop cultivar 'IH151343' when grown in Oregon's Willamette Valley.

| | Description |
|---|---|
| Trait | |
| Ploidy | 2X (diploid) |
| Plant | Vigorous climbing bine |
| Shape | Columnar |
| Foliage density | Medium |
| Target area | Oregon's Willamette Valley (USDA hardiness zone 8b near latitude 45 degree North) |
| Bine | |
| Shape | Hexagonal |
| Color | 143C, 143D |
| Striping Color | 175A, 178A, 178B |
| Total length (ft) | 18+ |
| Leaf Petiole | |
| Color | 144B with occasional 175A and 178A |
| Shape | Flat upper surface with channel |
| Leaf | |
| Arrangement | Opposite |
| Shape | Mix of cordate, 3-lobed, and 5-lobed |

TABLE 7-continued

Qualitative mid-canopy data collected from hop cultivar 'IH151343' when grown in Oregon's Willamette Valley.

| | Description |
|---|---|
| Color | Adaxial: NN137A<br>Abaxial: 191A |
| Venation | primary order: palmate<br>secondary order: craspedodromous |
| Vein color | 144B |
| Blistering | Absent |
| Leaf margin | Serrated |
| Ligule color | 144A & 144B |
| Adaxial leaf texture | pubescent |
| Abaxial leaf texture | pubescent |
| Cone | |
| Shape | Ovate |
| Flowering date | Typically July 10-20 |
| Maturity date | Late-August to early September |
| Coning abundance | Mid-canopy coning density: medium<br>Upper-canopy coning density: medium |
| Degree of cone opening | Closed |
| Petiole color | 143B |
| Bract color | 145A |
| Bracteole color | 145C |
| Rachis color | 145A |

Sensory Observations

Internal sensory evaluations of hop cones from 'IH151343' took place from October 2021-November 2023. These evaluations include dry rub analysis for aromatic character, and dry hopping in a neutral beer to assess aromatic and taste expression. Dry rub analysis involves vigorously rubbing dried cones together to rupture lupulin glands and release aromatic components which are subsequently analyzed and recorded by experienced personnel. Dry hop analysis involves adding dried hop cones into a neutral base beer, and after allowing the oil components to transfer into beer, hop flavor and aroma is evaluated in the final product. The primary sensory notes obtained from this sensory testing indicates that 'IH151343' consistently contributes juicy berry notes such as huckleberry. lingonberry. red currant, and goose berry. lychee, as well as the floral notes lilac, lavender, and rose.

I claim:

1. A new and distinct variety of hop plant named 'IH151343', substantially as illustrated and described herein.

* * * * *